US010555533B2

(12) United States Patent
Borriss et al.

(10) Patent No.: US 10,555,533 B2
(45) Date of Patent: Feb. 11, 2020

(54) SELECTION AND USE OF COLD-TOLERANT BACILLUS STRAINS AS BIOLOGICAL PHYTOSTIMULATORS

(71) Applicant: ABITEP GMBH, Berlin (DE)

(72) Inventors: Rainer Borriss, Glienicke (DE); Kristin Dietel, Berlin (DE); Paul Beifort, Berlin (DE)

(73) Assignee: ABITEP GmbH, Berlin (DE)

( * ) Notice: Subject to any disclaimer, the term of this patent is extended or adjusted under 35 U.S.C. 154(b) by 0 days.

(21) Appl. No.: 15/566,467

(22) PCT Filed: Apr. 13, 2016

(86) PCT No.: PCT/DE2016/000159
§ 371 (c)(1),
(2) Date: Oct. 13, 2017

(87) PCT Pub. No.: WO2016/165685
PCT Pub. Date: Oct. 20, 2016

(65) Prior Publication Data
US 2018/0139967 A1    May 24, 2018

(30) Foreign Application Priority Data
Apr. 14, 2015   (DE) .................. 10 2015 004 809

(51) Int. Cl.
*A01N 63/00* (2006.01)
*A01N 63/04* (2006.01)
*C12N 1/20* (2006.01)
*C05G 3/02* (2006.01)
*C12R 1/07* (2006.01)
*C05F 11/02* (2006.01)
*C05G 3/00* (2006.01)

(52) U.S. Cl.
CPC ............ *A01N 63/00* (2013.01); *A01N 63/04* (2013.01); *C05F 11/02* (2013.01); *C05G 3/00* (2013.01); *C05G 3/02* (2013.01); *C12N 1/20* (2013.01); *C12R 1/07* (2013.01)

(58) Field of Classification Search
None
See application file for complete search history.

(56) References Cited

FOREIGN PATENT DOCUMENTS

| CN | 102503623 | * | 6/2012 | |
| WO | WO-2016001125 A1 | * | 1/2016 | ............ A01N 43/40 |

OTHER PUBLICATIONS

Han et al.( Antagonistic activities of *Bacillus* spp. strains isolated from tidal flat sediment towards anthracnose pathogens *Colletotrichum acutatum* and *C. gloeosporioides* in South Korea, Plant Pathology Journal(Suwon, Republic of Korea), 2015, 31(2), 165/1-165/11) (Year: 2015).*
ASit-Kaki et al.(In vitro and in vivo Characterization of Plant Growth Environments of Eastern Algeria, Applied Biochemistry and Biotechnology, 2014, 172((4), 1735-46) (Year: 2014).*
Aleti et al.(Surfactinvariants mediate species-specific biofilm formation and root colonization in Bacillus, Environmental Microbiology (2016), 18(8), 2634-2645) (Year: 2016).*
International Search Report (PCT/ISA/210) dated Sep. 26, 2016, by the European Patent Office as the International Searching Authority for International Application No. PCT/DE2016/000159.
Written Opinion (PCT/ISA/237) dated Sep. 26, 2016, by the European Patent Office as the International Searching Authority for International Application No. PCT/DE2016/000159.
Gulati et al., "Plant Growth-Promoting and Rhizosphere-Competent *Acinetobacter rhizosphaerae* Strain BIHB 723 from the Cold Deserts of the Himalayas", Curr Microbiol, 2009, pp. 371-377, vol. 58.
Yadav of al., "Culturable diversity and functional annotation of psychrotrophic bacteria from cold desert of Leh Ladakh (India)", World J Microbiol Biotechnol, 2015, pp. 95-108, vol. 31.
Yadav et al., "Prospecting cold deserts of north western Himalayas for microbial diversity and plant growth promoting attributes", Journal of Bioscience and Bioengineering, 2014, pp. 683-693, vol. 119, No. 6.
Yadav et al., "Bioprospecting of plant growth promoting psychrotrophic Bacilli from the cold desert of north western Indian Himalayas", Indian Journal of Experimental Biology, Feb. 2016, pp. 142-150, vol. 54.

* cited by examiner

*Primary Examiner* — Alton N Pryor
(74) *Attorney, Agent, or Firm* — Buchanan Ingersoll & Rooney PC

(57) ABSTRACT

The invention relates to a biological product for increasing the yield of crop plants. The invention can be used in agriculture, horticulture and plant protection. The product for stimulating the growth of crop plants is characterized by containing a cold-tolerant *Bacillus* strain.

13 Claims, 13 Drawing Sheets

Figure 1:
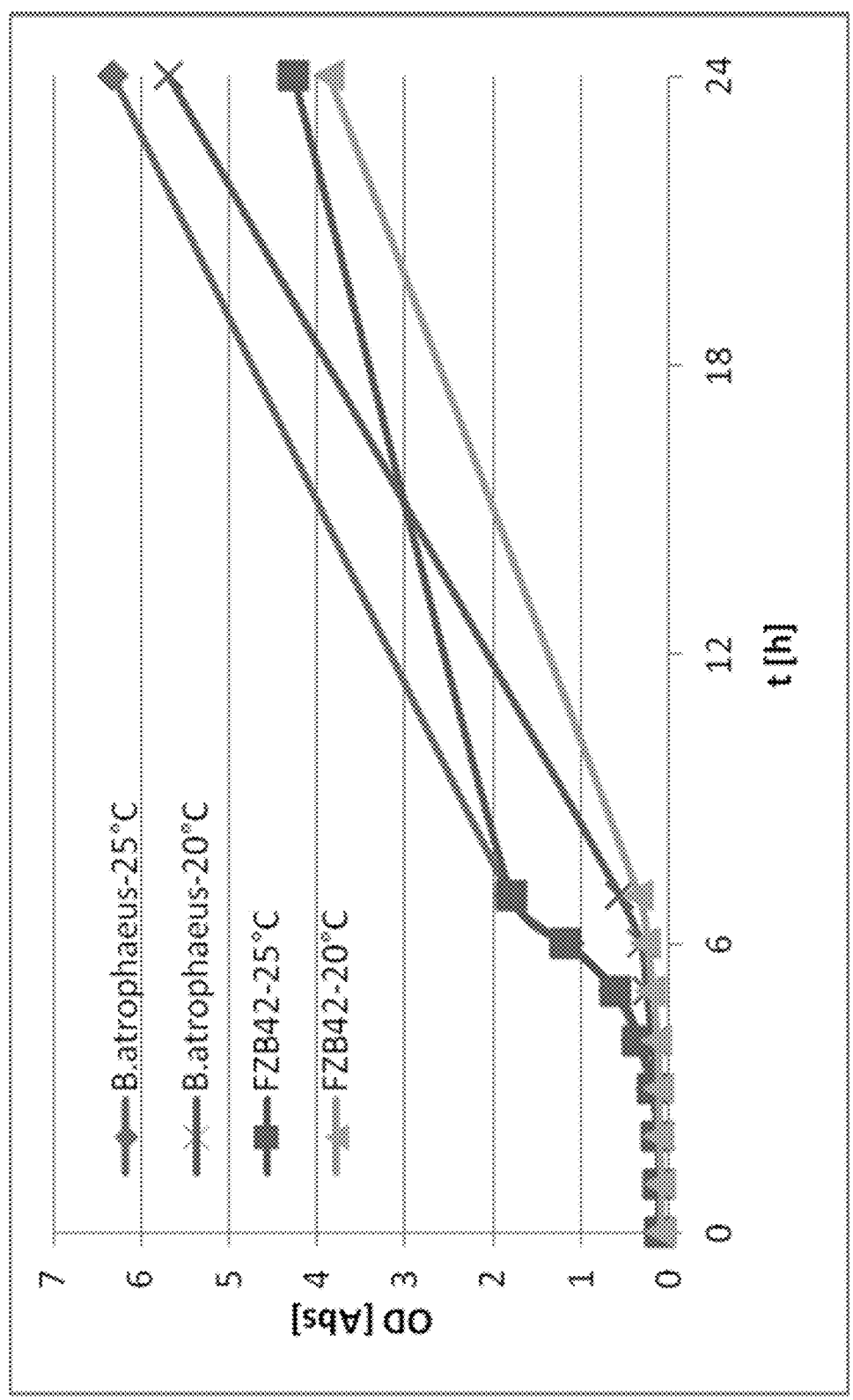

Specification includes a Sequence Listing.

SELECTION AND USE OF COLD-TOLERANT BACILLUS STRAINS AS BIOLOGICAL PHYTOSTIMULATORS

The invention relates to a biological means for improving the yield of cultivated plants. The areas of application of the invention are agriculture, horticulture and plant protection.

STATE OF THE ART

The introduction of biological plant protection and organic fertilisers is an environmentally, friendly alternative to chemical pesticides and mineral fertilisers. "Plant-growth-promoting" rhizobacteria (PGPR) are used for the production of effective organic formulae. Members of the *Bacillus* type with the ability to form permanent endospores are of great importance since they have a natural high degree of stability. Spores are permanent forms of the bacterial cell, which can withstand extreme environmental influences such as heat and aridity, and can be stored for years) without a loss of activity.

Organic formulae of members of the *Bacillus* type are the most frequently used biological plant protection and phytostimulators (Borriss 2011). Aside from the known producers of the insecticides *Bacillus thuringiensis* and *Bacillus kurstakii*, these are strains of the *Bacillus subtilis*, family incl. *B. amyloliquefaciens* subsp. *plantarum*, *B. subtilis*, *B. licheniformis* and *B. pumilus*, which are most commonly used in this field. Examples of commercial products (organic fertilizers and/or plant protection) that contain *B. amyloliquefaciens plantarum* spores are Kodiak™ (Bayer Crop Science), Companion (Growth Products Ltd.), BioYield™ (Bayer Crop Science), INTEGRAL® (BASF), VAULT® (BASF), SERENADE Max® (Bayer Crop Science), CEASE® (BioWorks, Inc.), RhizoVital® (ABiTEP GmbH), FZB24® (ABiTEP GmbH), Double Nickel 55™ (Certis U.S.A.), Amylo-X® (Certis U.S.A.). Plant protection based on *B. licheniformis* are Green Releaf and EcoGuard (Novozyme Biologicals Inc.). The *B. pumilus* GB34 strain (Yield Shield, Bayer Crop Science) is an active ingredient of organic fungicides. Other EPO-registered *B. pumilus* organic fungicides are SONATA (Bayer Crop Science), and GHA 180 (Premier Horticulture). Members of *B. mojavensis* have also been described as photostimulatory and capable of endophytic growth (Bacon & Hinton 2002). Other bacilli which do not belong to the *B. subtilis* species complex also stimulate plant growth and plant health. *B. firmus* GB126 (BioNem AgroGreen, Israel now taken over by Bayer Crop Science) is used as an EPO-registered nematicide for the organic control of phytopathogenic nematodes. A similar product from *B. firmus* Bmj WG is currently being developed by Certis U.S.A. A phytostimulatory *B. megaterium* (López-Bucio et al. 2007) strain is the basis for the BioArc organic fungicide. Members of the *Bacillus cereus* species complex, e.g. *B. cereus* UW8 (Handelsman et al. 1990), *B. thuringiensis* and *B. weihenstephanensis* have also been described as plant growth promoting, endospore-forming rhizobacteria.

These bacteria used for producing the current organic products are known as "mesophile" bacteria and require growth temperatures of over 15° C. in order to develop their effect as phytostimulators. More than 85% of the Earth's surface is covered by cold ecosystems, however, including Alpine mountain regions and areas that are oceanic and close to the poles (Feller & Gerday 2003). At temperature conditions below 15° C., which are typical for these regions, mesophile bacteria can have no positive effect on plant growth. An attractive alternative is the use of cold-tolerant microorganisms. Although their optimal growth conditions lie in the mesophile range, these microorganisms have developed mechanisms which give them the ability to continue to grow at lower temperatures ($\leq 10°$-$0°$ C.) (Kumar et al. 2010). A note was made that the use of cold-tolerant and plant growth promoting bacteria as inoculants, in particular for agricultural production in tempered climate zones with low temperatures and a short growth season can be attractive (Mishra et al. 2012). However, the known examples for the use of cold-tolerant bacteria in plant production on gram-negative phytostimulatory bacteria such as *Pseudomonas* (Katiyar & Goel 2003), *Burkholderia* (Barka et al. 2006), *Acinetobacter* (Gulati et al. 2009), *Azospirillum* (Kaushik et al. 2002), *Rhizobium* (Prevost et al. 2003), *Bradyrhizobium* (Zhang et al. 2003), *Pantoea* (Selvakumar et al. 2008a), *Serratia* (Selvakumar et al. 2008b). Although in the past, several psychrophile or cold-tolerant *Bacillus* types, such as *Bacillus globisporus* (now *Sporosarcina globisporus*), *Bacillus insolitus* (now: *Psychrobacillus insolitus*), *Paenibacillus macquariensis*, *Bacillus marinus* (now: *Marinibacillus marinus*), *Bacillus psychrophilus* (now: *Sporosarcina psychrophilus*), *Bacillus psychrosaccharolyticus*, *Bacillus psychrotolerans* (now: *Psychrobacillus psychrotolerans*) and *Bacillus psychrodurans* (now: *Psychrobacillus psychrodurans*) have been described (El-Rahman et al. 2002, Krishnamurti et al. 2010), there is a lack of information regarding *Bacillus* strains with a phytostimulatory effect.

GOAL AND OBJECTIVE OF THE INVENTION

The goal of the invention is to develop an environmentally sensitive and sustainable means for stimulating plant growth, including at temperatures below 15° C. The means should in particular be used in climatically unfavourable regions such as mountain regions and areas relatively close to the poles of the northern and southern hemisphere.

NATURE OF THE INVENTION

The object is attained according to the claim; subclaims 2-11 are preferred variants. The core of the invention is the use of cold-tolerant *bacillus* strains as biological phytostimulators. The scope of the invention further includes the combination of cold-tolerant *bacillus* strains with mesophile bacteria of the order Bacillales, preferably of type *Bacillus* and *Paenibacillus*, and the combination with humic acids. In the search for plant growth-promoting bacteria that show clear growth at temperatures below 15° C., it was found that endospore-forming bacilli that were isolated from cool climate regions such as mountain regions in the uplands of Tibet (People's Republic of China) or the Alpine foothills (1400 m) are also able to grow at temperatures below 12° C. In accordance with their 16S rNA sequences, these cold-adapted bacteria were assigned to the types *Bacillus simplex*, *Bacillus pumilus* and to the *Bacillus subtilis* species, complex. Due to their gyrA and cheA sequences, the members of the *B. subtilis* species complex were identified as belonging to the type *Bacillus atrophaeus*. The plant growth-promoting effect was examined with *Arabidopsis* seedlings in potted experiments. Cold-tolerant members of the types *Bacillus simplex*, *Bacillus atrophaeus* and *Bacillus pumilus* showed a clear phytostimulatory effect (example 6). The *B. simplex* (ABI02S1), *B. atrophaeus* (ABI02A1), and *B. pumilus* (ABI02P1) strains were selected as examples for further examinations. These strains are described below:

*Bacillus atrophaeus* differs from *B. subtilis* through its DNA sequence and the formation of a dark pigment (Nakamura 1989). Its ability to promote plant growth has been documented (Karlidag et al. 2010, Ertuk et al. 2011, Chan et al. 2013). The taxonomic affiliation of the strain ABI021A1 with *Bacillus atrophaeus* was determined by comparing its 16S rRNA, qyrA and cheA partial sequence (see example 1):

TABLE 1

| Primer | Gene fragment | Species | Accession | BLAST |
|---|---|---|---|---|
| pRB1601 | 16SrRNA | *B. atrophaeus* 1942 | CP002207.1 | 451/453 (99%) |
| pRB1602 | 16SrRNA | *B. atrophaeus* 1942 | CP002207.1 | 470/473 (99%) |
| gyrFW | gyrA | *B. atrophaeus* 1942 | CP002207.1 | 863/872 (99%) |
| gyrRV | gyrA | *B. atrophaeus* 1942 | CP002207.1 | 857/865 (99%) |
| cheAFW | cheA | *B. atrophaeus* 1942 | CP002207.1 | 604/698 (87%) |
| cheARV | cheA | *B. atrophaeus* 1942 | CP002207.1 | 509/533 (95%) |

ABI02A1, ABI03 and ABI05 are characterised by the following properties:

The physiological properties of BI02A1, ABI03 and ABI05 are shown in application example 3. The strains promote plant growth (see application example 1) and suppress the growth of bacterial (*Xanthomonas oryzae*) and fungal (*Sclerotinia sclerotorum*) pathogens in vitro. ABI02A1 was stored as strain DSM 32019, ABI03 was stored as strain DSM 32285 and ABI05 was deposited as strain DSM 29418 at the DSMZ, Braunschweig. *Bacillus atrophaeus* has already been described as a plant growth-promoting bacterium (Bai et al. 2002). To date, no reports have been made of a phytostimulatory effect at low temperatures with regard to *B. simplex*, however.

*Bacillus simplex* ABI02S1 and ABI12 already grow at 4° C. The growth maximum is 45° C. The physiological properties of the strain are shown in illustrative representation 4. Members of the *Bacillus simplex* species have currently been identified as phytostimulatory bacteria (Schwartz et al. 2013). To date, no reports have been made of a growth stimulation effect at low temperatures. The ABI02S1 strain was deposited as DSM 32020 and the ABI12 was deposited as DSM 32283 at the DSMZ Braunschweig, Germany.

The invention will now be explained in greater detail with reference to examples.

ILLUSTRATIVE EMBODIMENTS

Example 1: Isolation of Potential Cold-Tolerant Bacteria

Cold-tolerant *bacillus* strains were isolated e.g. from the uplands of the Autonomous Province of Tibet and the Alpine foothills, height 1,400 m. The Tibetan mountainous region lies at an average altitude of 4,000 m and has an annual average temperature of 10° C. Typical for this region are the large differences in temperature between day and night. The samples were either removed directly from plant roots or from the adhered earth:

2.5 g sample material were re-suspended in 25 g of distilled water for 2 h under continuous shaking. To kill vegetative cells, the suspension was then incubated for an hour at 80° C. 10 ml of the suspension were added to 40 ml of a mineral-salt medium and incubated for one week at 20° C. until under microscopic monitoring, rod-shaped cells emerged. Then, the suspension was diluted to $10^{-1}$ to $10^{-5}$ and plated on minimal agar. The plates were incubated at 20° C. and the colonies formed were separated on nutrient agar or LB agar.

The taxonomic classification of the isolates was achieved by determining their 16S rRNA sequence, and with strains from the related group of *subtilis* through their gyrA and cheA sequence. The isolation of the chromosome DNA of exponentially growing *bacillus* cells, DNA amplification and sequencing was conducted in accordance with Idriss et al. 2002. Here, the following primers were used to amplify the DNA sequences using polymerase chain reaction (PCR):

```
pRB1601:
5'GGATCCTAATACATGCAAGTCGAGCGG pRB1602:
5'GGATCCACGTATTACCGCGGCTGCTGGC gyrFW:
5'CAGTCAGGAAATGCGTACGTC gyrRV:
5'CAAGGTAATGCTCCAGGCATT cheAFW:
5'GAAACGGAKAYATGGMAGTBACMTCARACTGGCTG cheARV:
5'TGCTCRAGACGCCCGCGGWCAATGACAAGCTCTTC
```

An overview of the isolates obtained and their taxonomic classification on the basis of their 16S rRNA sequence is shown in Table 2.

TABLE 2

DNA sequences of cold-adapted *bacillus* isolates from the Tibetan uplands and the Alpine foothills (altitude 1,400 m)

| Strain | Place of isolation | Similarity with 16SrRNA | PGP[1] | Growth |
|---|---|---|---|---|
| ABI02S1 | Grass roots, Sejila Mountain, Nyingtri, Tibet | *B. simplex* 338/358 (94%) (pRB1601) *B. simplex* 403/464 (87%) (pRB1602) | + | 04-45° C. |
| ABI02A1 | Grass roots, Nyingtri, Tibet | *B. atropheus* 450/458 (98%) (pRB1601) *B. atrophaeus* 572/590 (97%) (gyrFW) *B. atrophaeus* 733/757 (97%) (gyrREV) | + | 10-45° C. |
| ABI02P1 | Namtso Lake, Lhasa, Tibet | *B. pumilus* 457/468 (98%) (pRB1602) | + | 10-50° C. |
| ABI03 | Grass roots, Alpine foothills, height 1,400 m | *B. atropheus* 446/465 (96%) (pRB1601) 474/475 (99%) *B. atrophaeus* 608/625 (97%) (gyrFW) (pRB1602) | + | 10-45° C. |

TABLE 2-continued

DNA sequences of cold-adapted *bacillus* isolates from the Tibetan uplands and the Alpine foothills (altitude 1,400 m)

| Strain | Place of isolation | Similarity with 16SrRNA | PGP[1] | Growth |
|---|---|---|---|---|
| ABI05 | Grass roots, Alpine foothills, height 1,400 m | *Bacillus atrophaeus* 450/458 (98%) (pRB1601) 447/478 (94%) (pRB1601) | + | 10-45° C. |
| ABI12 | Grass roots, Alpine foothills, height 1,400 m | *B. simplex* 450/472 (95%) (pRB1601) 461/472 (98%) (pRB1602) | + | 04-45° C. |

[1]PGP = plant growth promoting effect.

Example 2: Growth Characteristic of Cold-Tolerant Bacteria

The growth attempts were conducted in LB medium at different temperatures. Table 2 provides an overview of the growth behaviour of the cold-tolerant strains. The upper growth limit of *B. simplex* ABI02S1 and ABI12, and *B. atrophaeus* ABI02A1 ABI03 and ABI05 was 45° C., while *B. pumilus* ABI02P1 also grows at 50° C. *B. atrophaeus* and the mesophile *B. amyloliquefaciens* subsp. *plantarum* FZB42 were cultivated at 20° C. and 25°. At these temperatures, the cold-tolerant *B. atrophaeus* strain had a faster growth rate than FZB42 (FIG. 1).

Figure 2:
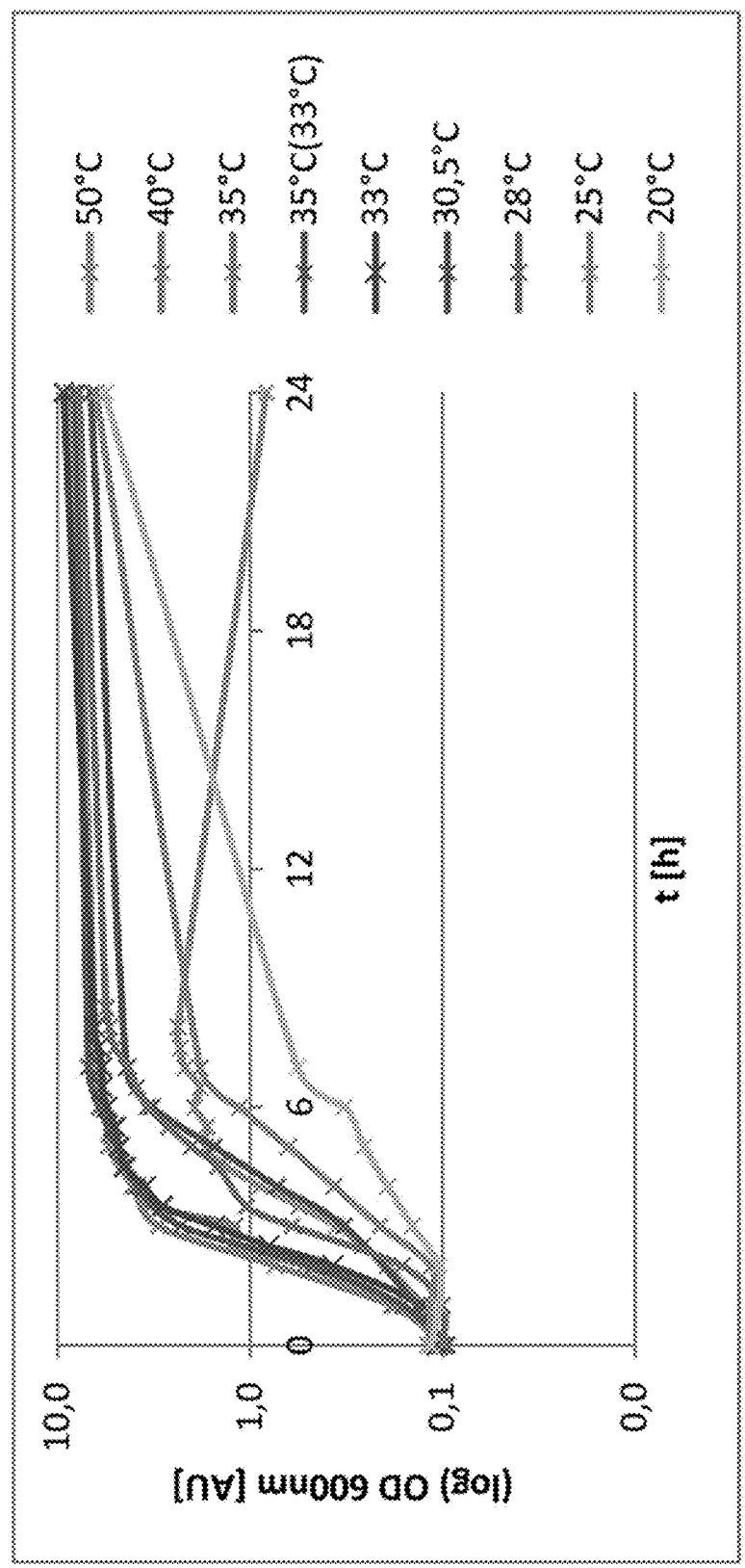

*B. atrophaeus* ABI02A1 was cultivated at different temperatures between 20° and 50° C. (FIG. 1). The growth optimum was determined at 33-35° C. At 30° C., a slight deceleration of growth speed was registered. Below 30° C., this effect was reinforced (25° C. and 20° C.). At 40° C., growth was significantly delayed. At 50° C., a lysis of the cells was also observed (FIG. 2). The results confirm that in the case of *B. atrophaeus* ABI02A1, this is a mesophile, but also cold-tolerant strain, which despite a growth optimum of 33-35° C. also grows well at low temperatures.

The physiological properties of the cold-tolerant *Bacillus atrophaeus* and *Bacillus simplex* strains are described in examples 3 and 4 below.

Example 3: Physiological Properties of *Bacillus atrophaeus*

TABLE 3

Physiological properties of *Bacillus atrophaeus* ABI02A1, ABI03 and ABI05

| The use of sugars | |
|---|---|
| Glucose | + |
| Saccharose | + |
| Lactose | − |
| Maltose | ± |
| Fructose | + |
| Voges Proskauer | + |
| Exoenzyme formation | |
| Lipase (tributyrin) | + |
| Amylase (starch) | + |
| Protease (casein) | + |
| Keratinase (keratin) | − |

TABLE 3-continued

Physiological properties of *Bacillus atrophaeus* ABI02A1, ABI03 and ABI05

| The use of sugars | |
|---|---|
| Cellulase (cellulose) | − |
| Egg yoke test (lecithinase) | − |
| Pigment formation | + |
| Inhibition by antibiotics (flake test) | |
| CM5 chloramphenicol | + |
| KM5 kanamycin | +++ |
| ERI erythromycin | ++ |
| Li25 lincomycin | + |
| AP100 ampicillin | ++ |
| RIF 25** rifampicin | +++ |
| SPEC 100 spectinomycin | ++ |
| Bleo1 bleomycin | + |

In contrast to *B. amyloliquefaciens* subsp. *plantarum* FZB42, *Bacillus atrophaeus* ABI02A1, ABI03 and ABI05 also grow at 10° C. At 20° C. and 25° C., ABI02A1 also has a higher growth speed than FZB42 (FIG. 2). In the agar diffusion test, ABI02A1, ABI03 and ABI05 inhibit *Bacillus subtilis*, *Bacillus megaterium*, and the phytopathogens *Erwinia amylovora*, *Xanthomonas oryzae*, *Fusarium oxysporum*, *Rhizoctonia solani* and *Sclerotinia scierotiorum*.

Example 4: Physiological Properties of *Bacillus simplex*

*B. simplex* ABI02S1 and ABI12 have the following physiological properties (Table 4).

TABLE 4

Physiological properties of ABI02S1 and ABI12

| Cell form | Rod, 0.9-1.0 × 3.0->4.0 m |
|---|---|
| Endospores | Ellipsoid |
| Spore parent cell | Not swollen |
| Use of citric acid | + |
| Use of propionic acid | − |
| Catalase | + |
| Nitrate reductase (NO$_2$ from NO$_3$) | + |
| Phenylalanin desaminase | − |
| Arginin dihydrolase | − |
| Indole formation | − |
| Anaerobic growth | − |
| Voges Proskauer (acetone formation) | − |
| pH in Voges Proskauer medium | 6.2 |
| Lecithinase (egg yoke reaction) | − |
| Growth at 50° C. | − |
| Growth at 45° C. | (+) |
| Growth at 40° C. | + |
| Growth at pH 5.7 | − |
| Growth at 2% NaCl | + |
| Growth at 5% NaCl | − |
| Growth at 7% NaCl | − |
| Growth at 10% NaCl | − |
| Acid formation of D-glucose | + |
| Acid formation of L-arabinose | + |
| Acid formation of D-xylose | + |
| Acid formation of D-mannite | + |
| Acid formation of D-fructose | + |
| Gas of D-glucose | − |
| Hydrolysis of starch | + |
| Hydrolysis of gelatine | + |
| Hydrolysis of casein | + |
| Hydrolysis of Tween 80 | + |
| Hydrolysis of aesculin | (+) |

The physiological properties largely confirm the assignment to *Bacillus simplex*, but are not typical for *Bacillus simplex* for all features. The analysis of the cellular fatty acids shows a typical profile for the *bacillus* type.

*B. simplex* ABI02S1 and ABI12 grow in LB medium at 10° C., a temperature at which *B. amyloliquefaciens* FZB42 can no longer grow. In further experiments, it was shown that these two *B. simplex* strains can also grow at a temperature of 4° C. The growth maximum was 45° C.

In the agar diffusion test, *B. simplex* had a suppressive effect on the pathogenic funghi *Rhizoctonia solani* and *Fusarium oxysporum*, and on *Xanthomonas otyzae*.

Example 5: Fermentation of *Bacillus atrophaeus* ABI02A1 and the Production of a Spore Suspension For example, a' description is given here for the production of a spore suspension for *B. atrophaeus* ABI02A1. The fermentation of *B. atrophaeus* was conducted in a conventional stirring fermenter with a base volume of 1.4 l medium under the following conditions:

Medium: Full medium with organic N and C source: Soya flour or maize steeping liquor, low fat milk powder, yeast extract, salts
  Sterilisation of the medium: 20 mins. at 121° C.
  Template anti-foam agent: 200 ml
  Stirrer speed: 700 RPM.
  Fermentation temperature: 33° C.
  Ventilation: 0.7 l/min (40% $O_2$ saturation)
  pH: with NaOH set to 6.9

After 16 h, a maximum cell density of $1 \times 10^{10}$ cells/ml was achieved. The culture was continued in order to achieve the most complete possible sporing of the vegetative cells. After 40 h, a spore titer of $3 \times 10^9$ was achieved. The spores were centrifuged out and transferred to 10% of the original medium volume, under addition of propandiol (final concentration: 5%).

Example 6: Promotion of Germination of Maize Seeds Through Cold-Tolerant Bacillae 10 ml of a *bacillus* spore suspension were mixed with 30 ml 1% carboxymethyl celluluse (CMC), which served as an adhesive for improved adhesion of the spores to the maize surface. The final concentration of the *bacillus* spores in the suspension was $1 \times 10^7$, $1 \times 10^6$, $1 \times 10^5$, $1 \times 10^4$ cfu/ml. The maize seeds were surface-disinfected with 75% ethanol, 5% NaClO for 5 mins., before they were treated with the different dilutions of the *bacillus* spore suspension for 5 mins. In each case, 3×10 seeds of a spore concentration were laid out in a petri dish with damp filter paper. The germination rate was determined after a week of dark incubation at 30° C. As a control, maize grains were used which had been treated with a sterile nutrient medium+CMC.

Figure 4:
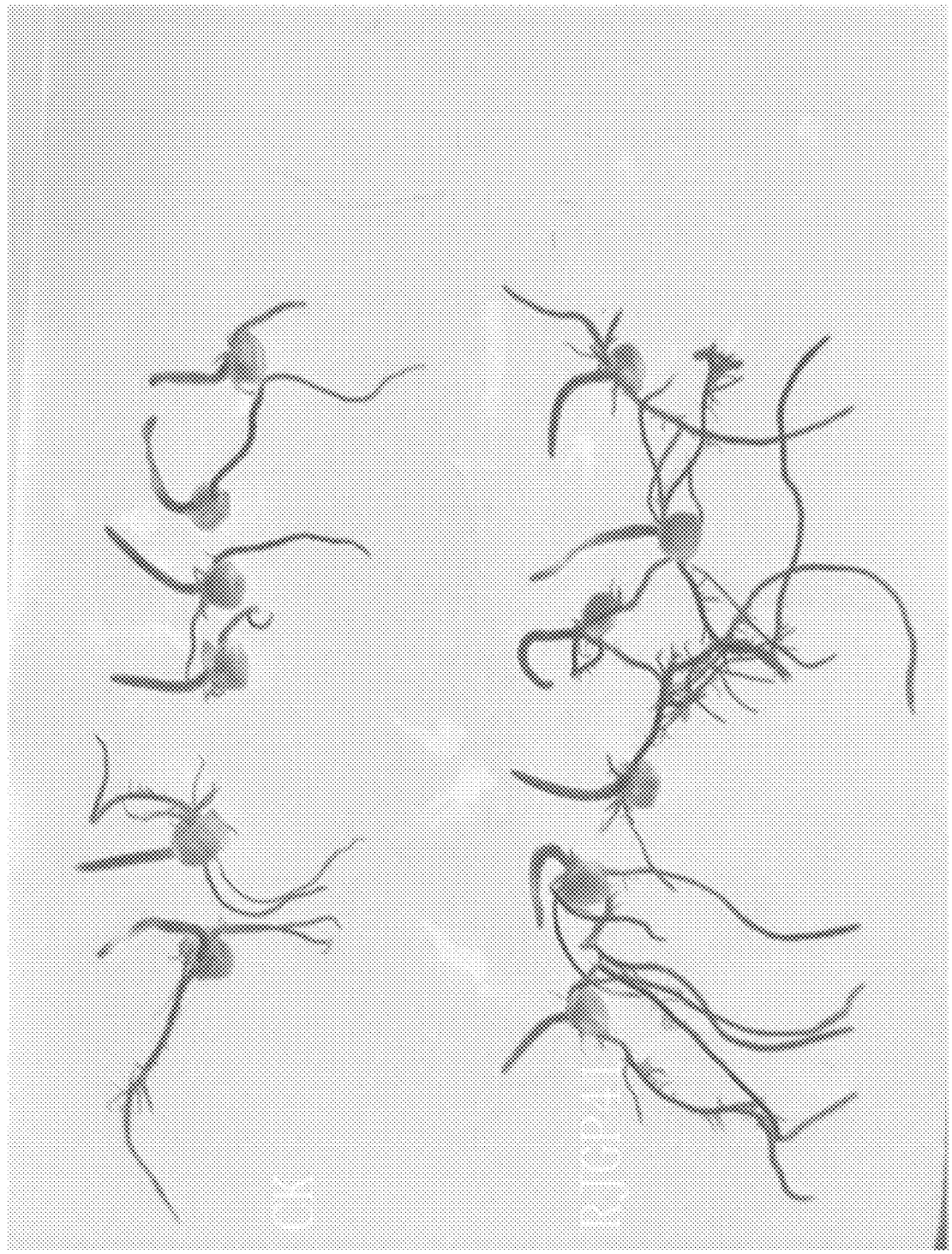

A clear increase in germination speed was determined with the application of *B. simplex* and *B. atrophaeus* (FIG. 4).

Example 7: Growth Experiments with *Arabidopsis thaliana*

Figure 5:
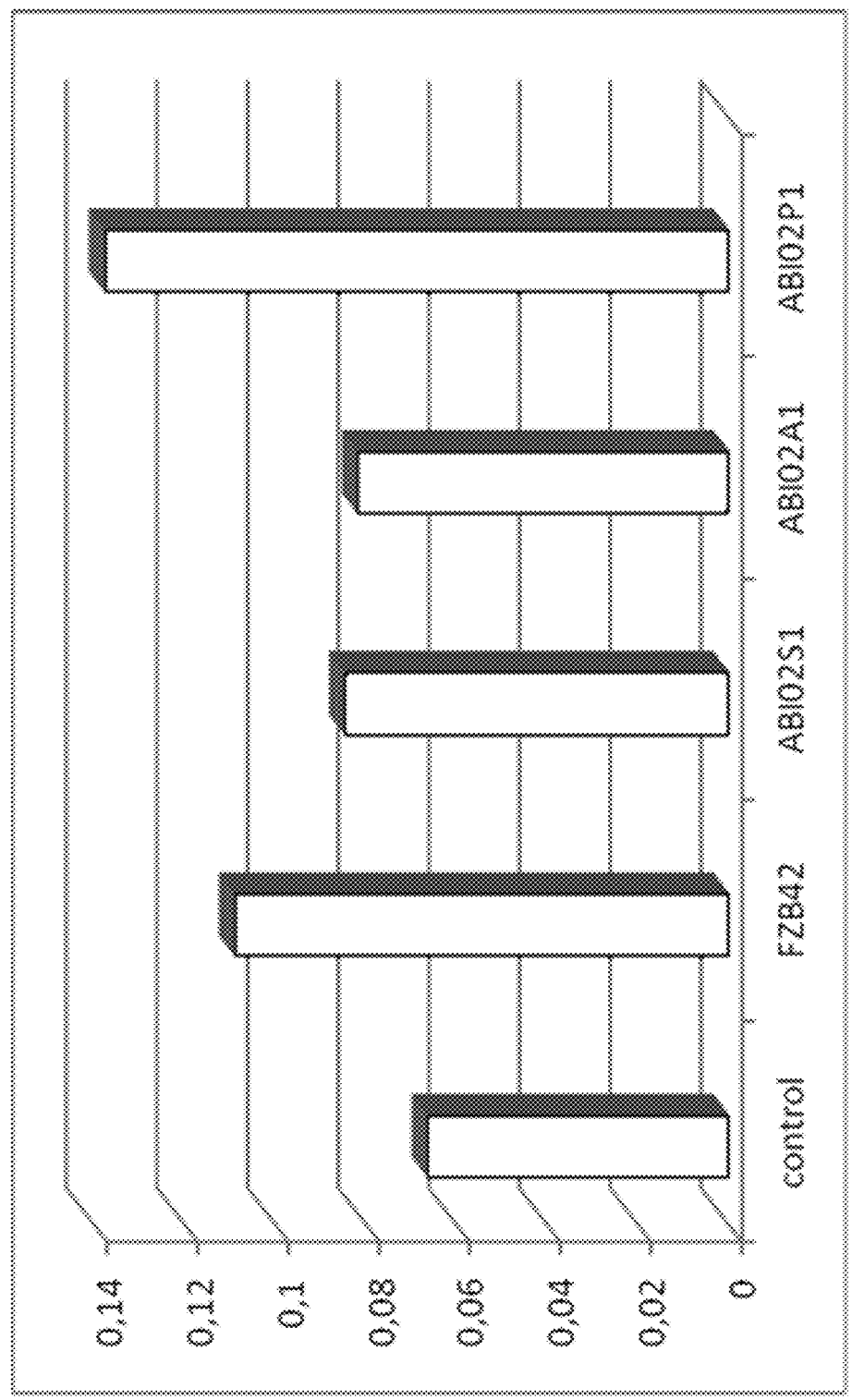
Figure 6:
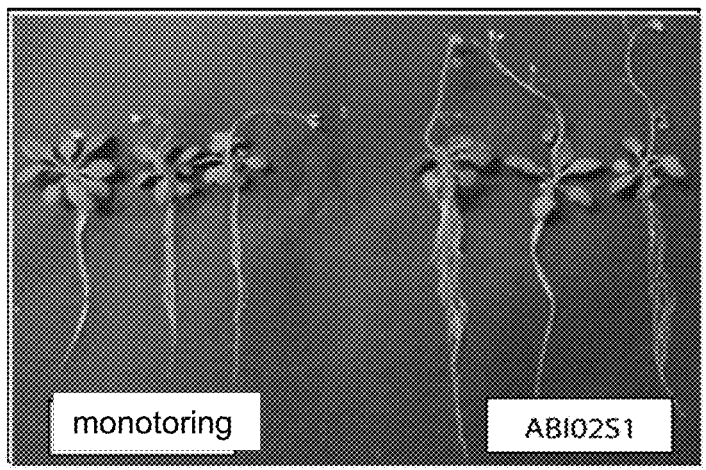
Figure 6:
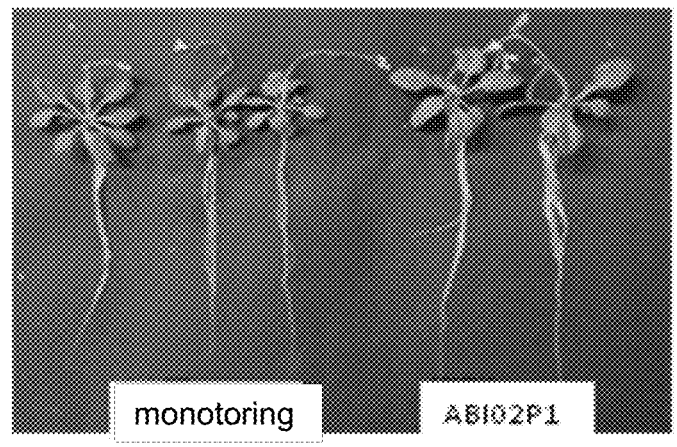
Figure 6:
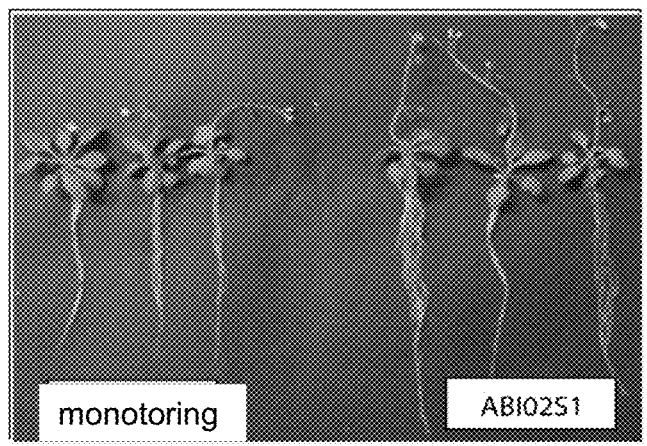

The roots of a 6-day-old *Arabidopsis thaliana* seedling were incubated for 5 mins. in a spore suspension ($10^5$ spores/mil) of cold-adapted bacillae. For comparison, a treatment with a spore suspension of FZB42, which is known for its growth-promoting effect, was conducted. Then, the treated seedlings were transferred to Murashige-Skoog (MS) agar (1%). The quadratic plates (12×12 cm) were closed with parafilm and kept for three weeks at 23° C. (8/16 light-dark rhythm). Then, the fresh weight of the *Arabidopsis* plants was determined. Cold-tolerant members of the types *Bacillus simplex*, *Bacillus atrophaeus* and *Bacillus pumilus* showed a clear phytostimulatory effect (FIG. 5, FIG. 6).

Example 8: Potted Test with Potato Plants in a Greenhouse

Figure 7:
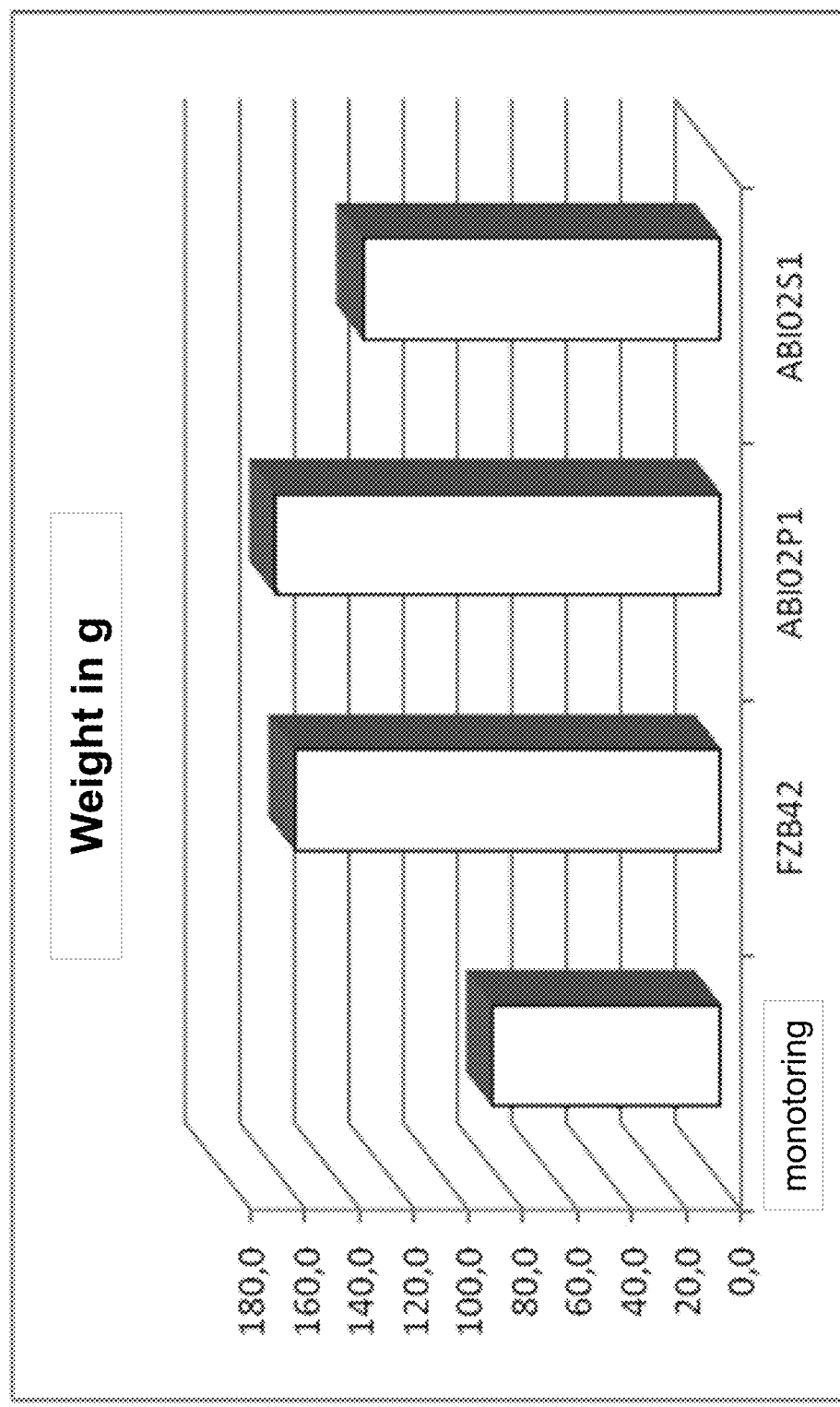

The test was conducted at the test facility for potato research, Agro Nord, D-18190 Groβ-Lüsewitz as a potted test from Nov. 7-10, 2011. The tubers of the potato test plant, of type "Burana", was infested with symptoms of a *Rhizoctonia solani* attack ("black scurf", "pocks"). The tubers were "stained" before planting with a diluted spore suspension of the *bacillus* formulae. The planting was conducted after the tubers had dried. The potatoes were harvested three months after planting. The rating of the potato plants and tubers showed a reduction of the *Rhizoctonia* infestation compared to the control of 40-45% with the variants treated with *Bacillus pumilus* ABI02P1 and *Bacillus simplex* ABI02S1. At the same time, a yield increase of 95% (ABI02P1) and 57% (ABI02S1) was achieved (FIG. 7). The results achieved with the use of the cold-tolerant strains are thus comparable with the results achieved with the use of FZB42. Here, it should be taken into account that the test was conducted in the summer and early autumn, when the average daytime temperatures are by no mewls optimal for the use of cold-tolerant bacteria.

Example 9: Field Test, Potatoes with *B. pumilus* and *B. simplex*

Figure 8:
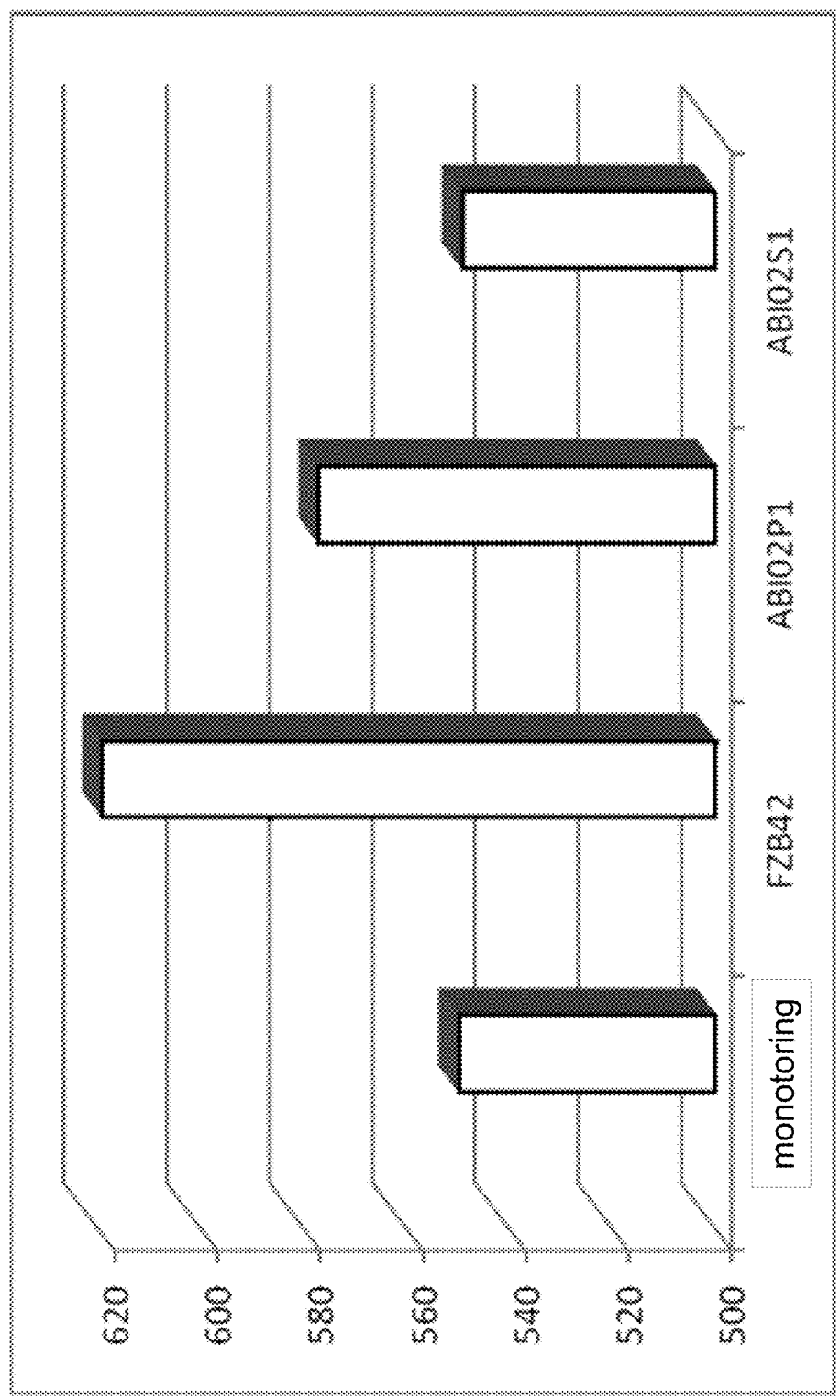

See the example below for information on the test procedure. The staining of the potato tubers with the mesophile, plant growth promoting bacterium FZB42 led to an increased yield compared to the untreated control of 14% (quantity used: 1 l spore suspension/ha). The increase in yield through staining with the cold-tolerant *Bacillus pumilus* ABI02P1 (quantity used: 1 l spore suspension/ha) was 6% compared to the untreated control. No increase in yield was achieved with the use of a spore suspension of the cold-tolerant *Bacillus simplex* ABI02S1 (FIG. 8). When interpreting the results, it should be taken into account that the test was conducted from May to September, when the average daytime temperatures are by no means optimal for the use of cold-tolerant bacteria.

Example 10: Field Test: The Use of *Bacillus atrophaeus* (ABI02A1) Leads to an Increase in Yield with Potatoes The field test was conducted by Agro Nord, Prüstelle für Kartoffelforschung, 18190 Groβ Lüsewitz, in Sanitz (Mecklenburg-West Pomerania). Preceding crop: maize. Soil type/number IS/35, fertilisation: 140 kg N. The potato type "Verdi" (medium-late-late) was used. The spore suspension was applied using injection (lot injection PL1, nozzle type: Flat jet nozzles TJ 800 15). Here, the spore suspensions used ($2 \times 10^{13}$ spores/l) were diluted in 300 l of water before use. The "staining" was conducted on May 5, 2013 in the storage building. Following successful drying of the tubers, they were planted on Jun. 5, 2013 at a soil temperature of 15.8° C.

Climatic conditions: The month of May was too warm by 1.2° C., and too damp by 42.5 mm (79%). These were good emergence conditions for the potatoes. The month of June generally matched the average values recorded for a period of many years. However, precipitation primarily occurred in the form of heavy rain (13th=26 mm; 20th=14.3 mm; 25th=13.5 mm) approx. 74% of the precipitation total for the month. The only significant precipitation in July occurred on 3rd July with 28.4 mm; it was followed by a very long dry period, which continued until the end of August combined with too high temperatures.

Figure 10:
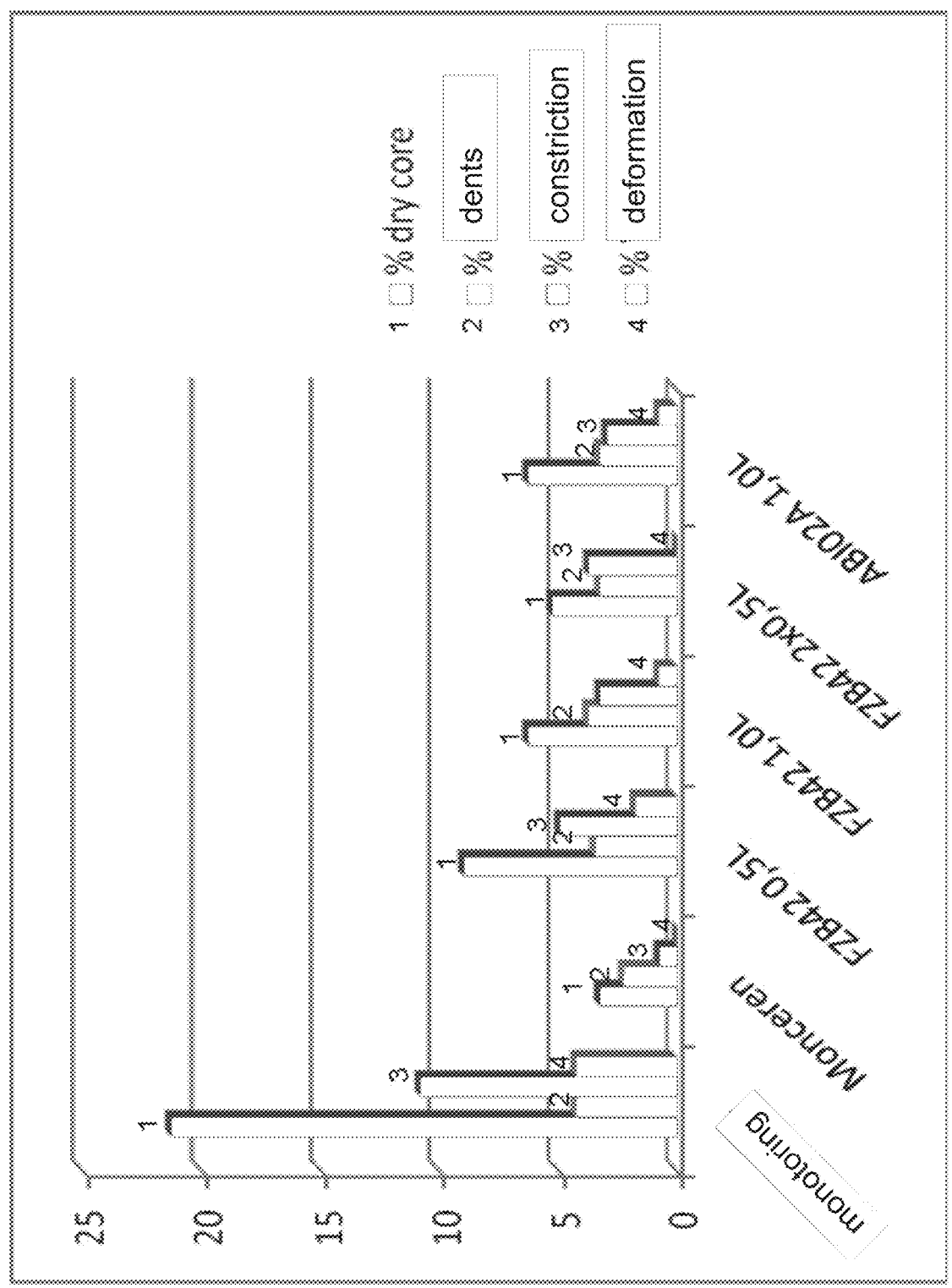

The test was influenced by the occurrence of the phytopathogen, ground level fungus *Rhizoctonia solani*. *Rhizoctonia solani* J. G. Kühn is the amorphous form of *Thanatephorus cucumeris* (A. B. Frank) Donk (teleomorph), a basidiomycete from the Agaricales family. It leads to yield losses (loss of emergence, necroses on stalks and stolons, many small or misshapen tubers) and quality losses (potato pocks, "dry core" symptoms). The antagonistic effect of *B. atrophaeus*, FZB42 and the chemical fungicide Monceren Pro was determined (FIG. 10).

The use of a spore suspension ($2\times10^{10}$ cfu/ml) of *Bacillus atrophaeus* (ABI02A1) in a concentration of 1.0 l/ha leads to a reduction in disease symptoms of "black scurf" (dry core) and an increase in yield of 10%. Thus the effect of this organic phytostimulator corresponds to that of the chemical fungicide Monceren Pro (concentration: 1.5 l/ha).

Example 11: Field Test: Confirmation: The Use of *Bacillus atrophaeus* (ABI02A1) Leads to an Increased Yield for Potatoes and a Reduced Infestation of *Rhizoctonia solani* (Kuerzinger 2014)

Figure 12:
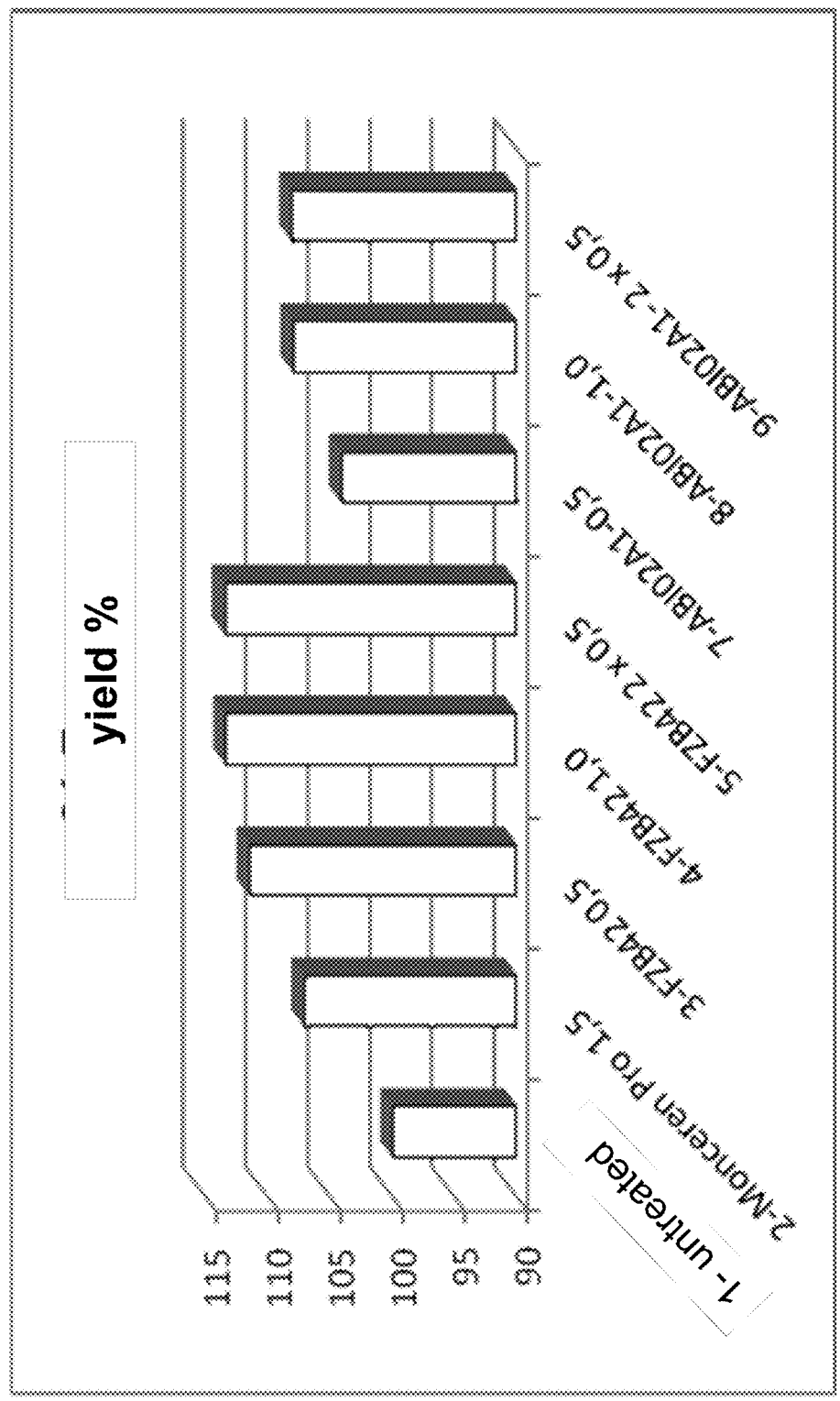
Figure 13:
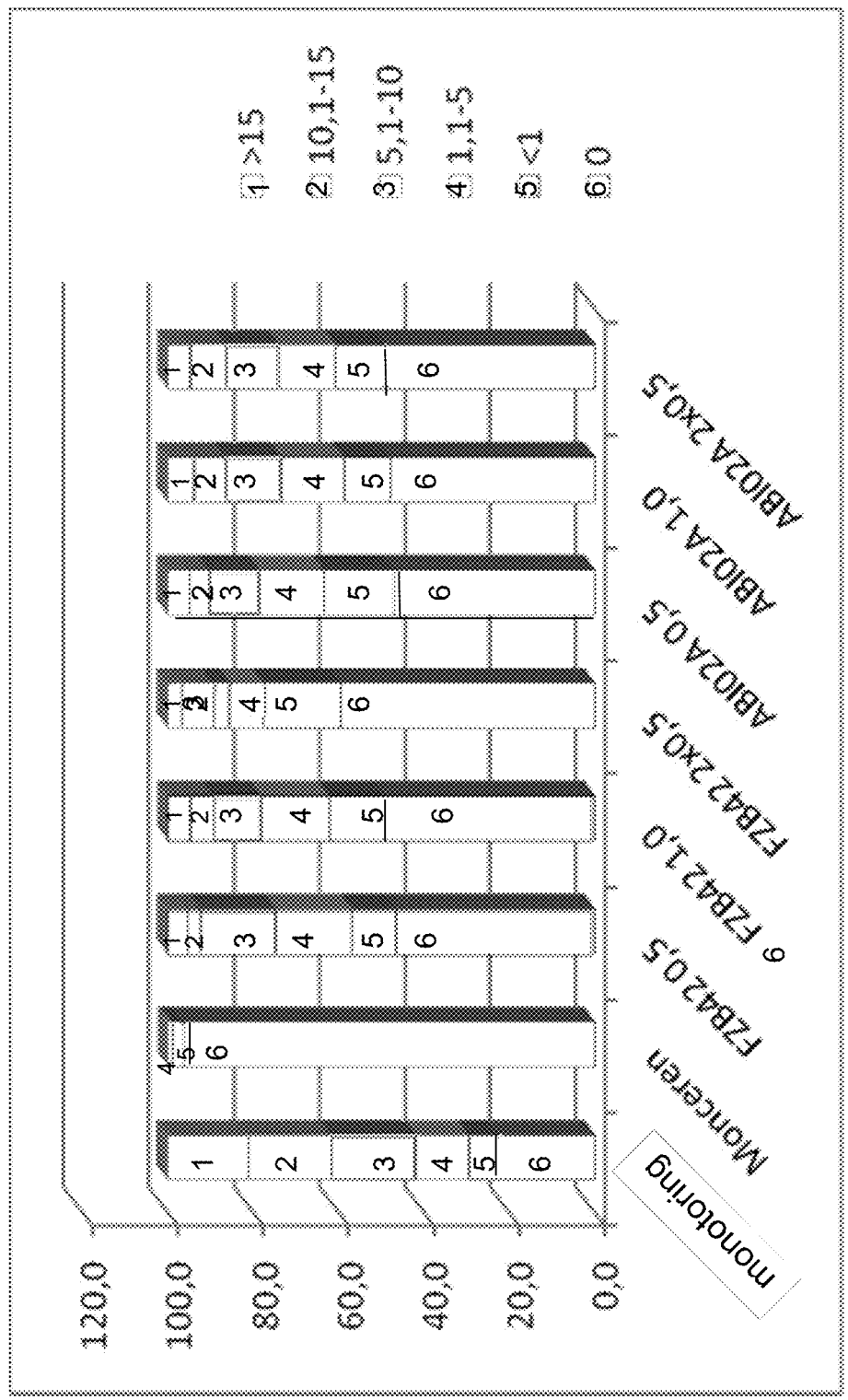

In a second test series (Kürzinger 2014), the results of example 10 were confirmed. The effect of *B. atrophaeus* ABI02A1 spore suspensions was comparable with that of the chemical fungicide Monceren (FIG. 12 and FIG. 13).

LEGEND FOR THE FIGURES

FIG. 1: Comparison of the growth of *B. atrophaeus* ABI02A1 and the mesophile strain FZB42 at 20° C. Viand 25° C.

FIG. 2: Growth of *B. atrophaeus* ABI02A1 at different temperatures. The growth optimum was determined at 33-35° C.

Figure 3:
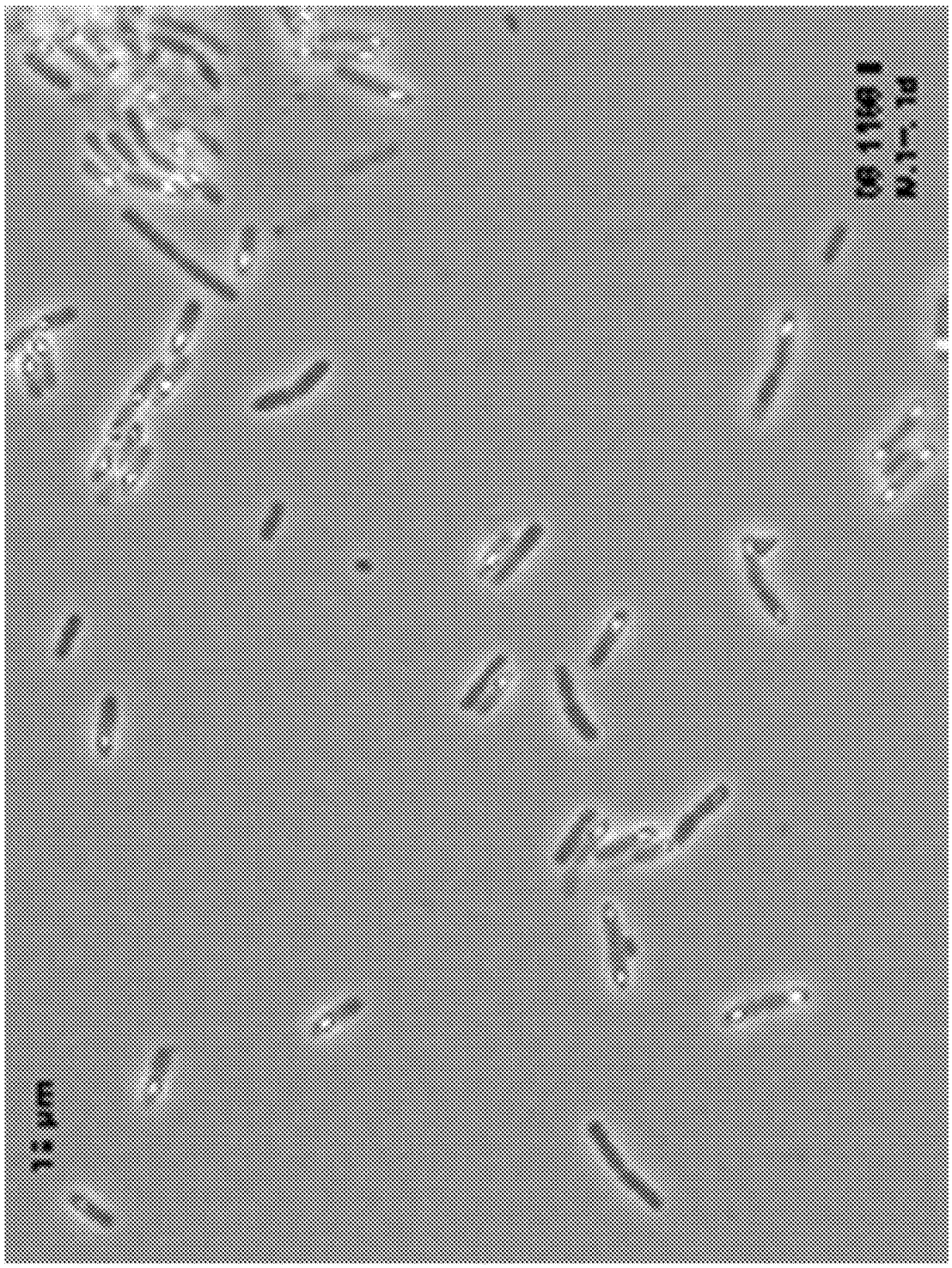

FIG. 3: Phase contrast: *Bacillus simplex* ABI02S1. The distal, oval endospores are clearly visible in the non-swollen spore parent cells.

FIG. 4: Improved germination of *Zea mays* following incubation with *B. simplex* ABI02A1 (bottom row) compared to the control.

FIG. 5: Growth stimulation (in g fresh weight) of *Arabidopsis thaliana* through spore suspensions of cold-tolerant *Bacillus* strains. In comparison: The effect of *B. amyloliquefaciens* FZB42. Control: without inoculation of *Bacillus* spores. The columns show the average value of three independent tests.

FIG. 6: Stimulation of root growth of *Arabidopsis thaliana* by *B. atrophaeus* ABI02A1 (upper left), and *B. simplex* ABI02S1 (upper right). CK=Control without inoculation with bacteria FIG. 7: Potted test with potato plants (Kurzinger GmbH 2011). Comparison of the tuber yield with untreated control. Application of 1 l spore suspension per ha of FZB42 and *B. pumilus* ABI02P1. The spore suspension of *B. simplex* ABI02S1 showed a lower concentration by a factor of 5, and was applied in a correspondingly higher quantity (5 l/ha) to the potato plants.

FIG. 8: Application of *B. pumilus* ABI02P1 (1 L/ha) and *B. simplex* ABI02S1 to potato plants. Single application through staining with the spore suspension (FZB42 and *Bacillus pumilus* ABI02P1: $2\times10^{10}$ cfu/ml, *Bacillus simplex* ABI02S1: $4\times10^9$ cfu/ml) before planting)

Figure 9:
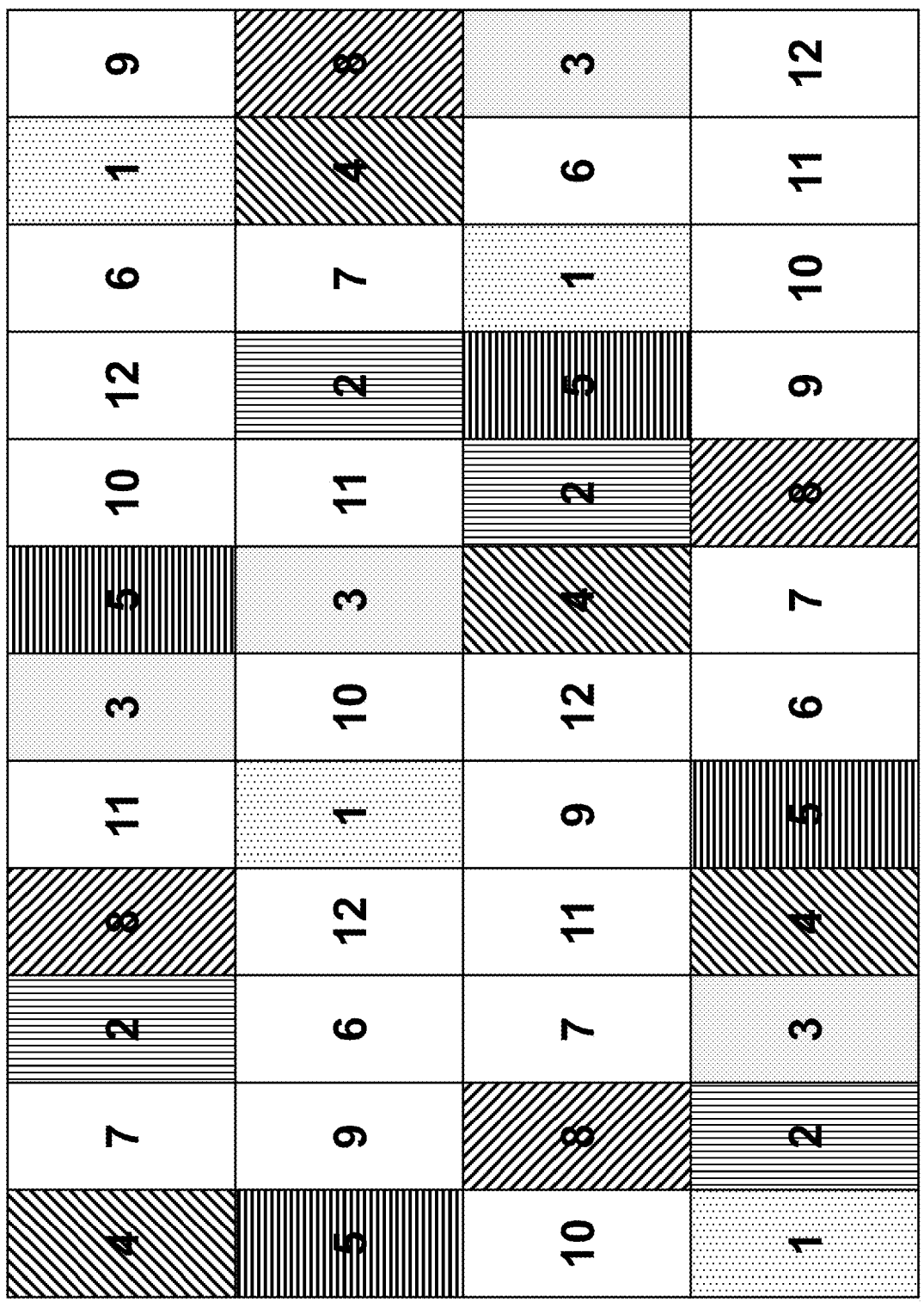

FIG. 9: Randomised location map: 1 (control, no addition), 2 chemical fungicide (Monceren Pro) 1.5 l/ha), 3 FZB42 (0.5 l/ha), 4 FZB42 (1.0 l/ha), 5 FZB42 ($2\times0.5$ l/ha), 8 ABI02A (1 l/ha). For each variant, four repetitions were conducted. The lot size was as follows: 6.90 m×3.00 m=20.70 m², space between rows: 75 cm, space between tubers in the row: 30 cm. "Staining" of the tubers in the storage building: 0.5.2013, date planted: 6 May 2013, emergence date: 2 Jun. 2013, harvest: 30 Aug. 2013, treatment: 7 Oct. 2013.

FIG. 10: Reduction in disease symptoms ("black scurf") following application of chemical fungicides (Monceren Pro) and organic stimulators. The use of ABI02A '*Bacillus atrophaeus*' (1.0 l/ha) leads to a considerable reduction in disease symptoms.

Figure 11:
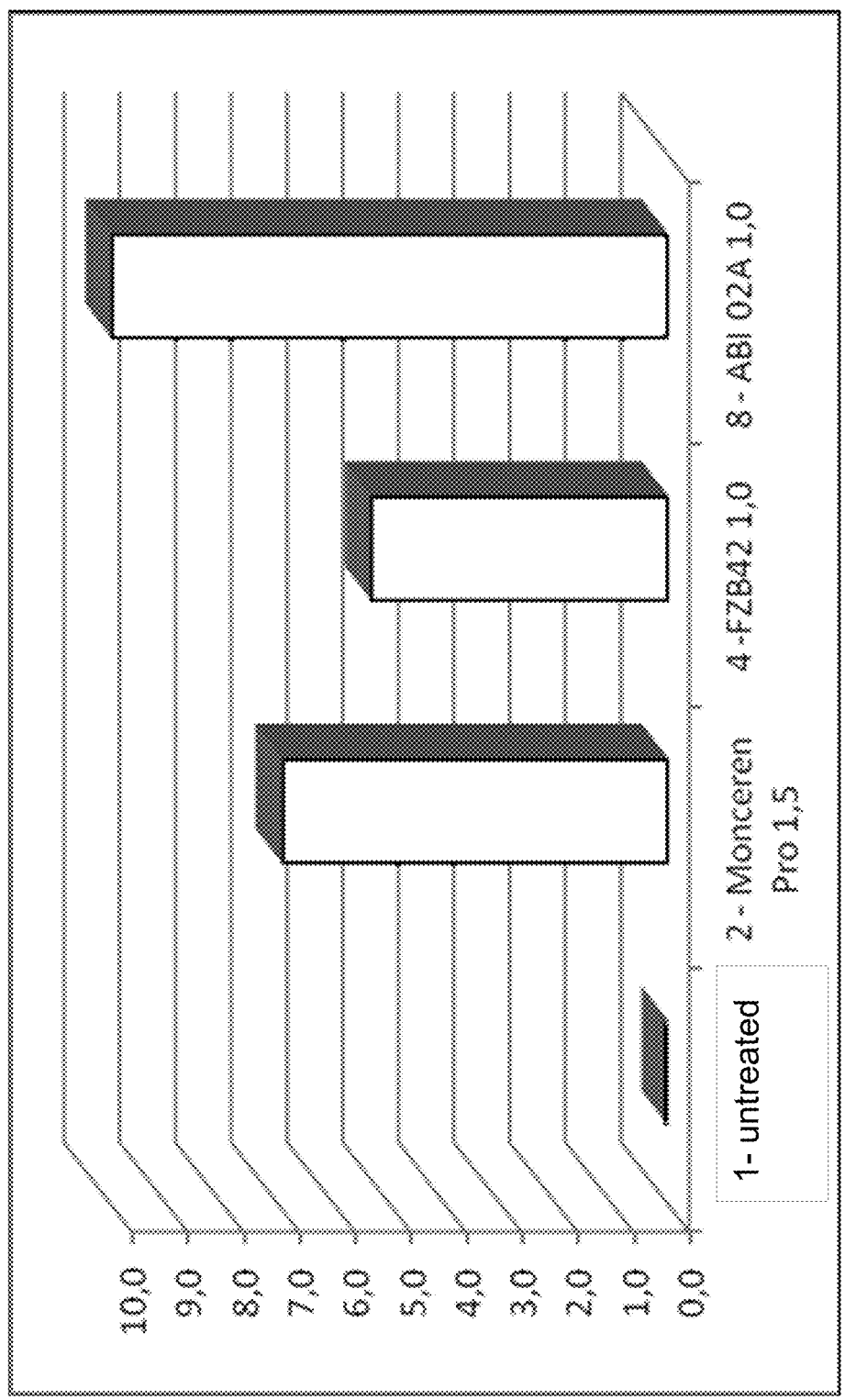

FIG. 11: The use of Monoceren (chemical fungicide) and spore suspensions of FZB42 and ABI02A1 (*Bacillus atrophaeus*) among potatoes of type Verdi (Sanitz, Kürzinger 2013) leads to an increase in yield (%). Quantities used: 1.0=1.0 kg/ha.

FIG. 12: The application of *Bacillus atrophaeus* ABI02A1 leads to a considerable increase in yield, which can be compared to that of the chemical fungicide Monoceren. With the mesophile strain FZB42, a somewhat higher yield increase was achieved. Quantities of fungicides used: 1.5 l/ha (Monceren), 0.5 1.0 l/ha and 2×0.5 l/ha with spore suspensions of FZB42 and ABI02A1.

FIG. 13: At the same time, the infestation of sclerotia (*Rhizoctonia solani*) was reduced with the application of *Bacillus atrophaeus* ABI02A1 compared to the untreated control. Illustration of all infestation classes (% sclerotia infestation) with the use of Monoceren, FZB42 and *B. atrophaeus*. *B. atrophaeus* leads to a reduction in sclerotia infestation compared to the untreated control. Infestation classes: 0, <1, 1.1-5, 5.1-10, 10.1-15 and >15.

LIST OF REFERENCES

Abd El-Rahman, Fritze, D., Cathrin Sproer, C., Claus, D. 2002. Two novel psychrotolerant species, *Bacillus psychrotolerans* sp. nov. and *Bacillus psychrodurans* sp. nov., which contain ornithine in their cell walls. Int. J. Syst. Evol. Microbiol. 52, 2127-2133

Bai, Y., D'Aoust, F., Smith, D. L., Driscoll, B. T. 2002. Isolation of plant-growth-promoting *Bacillus* strains from soybean root nodules. Can. J. Microbiol. 48, 230-238 (2002)

Barka, A. E., Nowk, J., Clement, C. 2006. Enhancement of chilling resistance of inoculated grapevine plantlets with plant growth promoting rhizobacteria *Burkholderia phytofermans* strain PsJN. Appl Environ Microbiol 72:7246-7252

Benhamou, N, Kloepper, J. W., Quadt-Hallman, A., Tuzun, S. 1996. Induction of defense-related ultrastructural modifications in pea root tissues inoculated with endophytic bacteria. Plant Physiol. 112, 919-929

Borriss, R. 2011. Use of plant-associated *Bacillus* strains as biofertilizers and biocontrol agents, In: Maheshwari D K (ed). Bacteria in agrobiology: plant growth responses. Springer, Germany, pp 41-76

Chan, W. Y., Dietel, K., Lapa, S. et al. 2013. Draft Genome Sequence of *Bacillus atrophaeus* UCMB-5137, a Plant Growth-Promoting Rhizobacterium. Genome Announcement 1, e00233-13

Erturk, Y., Cakmakci, R., Omur Duyar, O., Turan, M. 2011. The Effects of Plant Growth Promotion Rhizobacteria on Vegetative Growth and Leaf Nutrient Contents of Hazelnut Seedlings (Turkish hazelnut cv, Tombul and Sivri). Int. J. Soil Science, 6, 188-198.

Feller, G. & Gerday C. 2003. Psychrophilic enzymes: hot topics in cold adaptation. Nature Reviews Microbiology 1, 200-208

Gulati, A., Vys, P., Rai, P., Kasana, R. C. 2009. Plant growth promoting and rhizosphere-competent *Acinetobacter rhizosphaerae* strain BIHB 723 from the cold deserts of the Himalayas. Curr. Microbiol. 58, 371-377

Handelsman, J., Raffel, S., Mester, E. H. et al. 1990. Biological control of damping-off of alfalfa seedlings with *Bacillus-cereus* UW85. Appl. Env. Microbiol. 56, 713-718

Katiyar, V., Goel, R. 2003. Solubilization of inorganic phosphate and plant growth promotion by cold tolerant mutants of *Pseudomonas fluorescens*. Microbiol Res 158, 163-168

Idriss, E. E., Makarewicz, O., Farouk, A. et al. 2002. Extracellular phytase activity of *Bacillus amyloliquefaciens* FZB45 contributes to its plant-growth-promoting effect. Microbiology 148, 2097-2109.

Kaushik, R., Saxena, A. K., Tilak, K. V. B. R. 2002. Can *Azospirillum* strains capable of growing at a suboptimal temperature perform better in field-grown-wheat rhizosphere. Biol Fertil Soils 35, 92-95

Karlidag, H., Esitken, A., Yildrim, E. et al. 2010. Effects of plant growth promoting bacteria on yield, growth, leaf water content, membrane permeability, and ionic composition of strawberry under saline conditions. J. Plant Nutr. 34, 34-45

Krishnamurti, S., Ruckmani, A., Pukall, R., Chakrabarti, T. 2010. *Psychrobacillus* gen. nov. and proposal for reclassification of *Bacillus insolitus* Larkin & Stokes, 1967, *B. psychrotolerans* Abd-El Rahman et al., 2002 and *B. psychrodurans* Abd-El Rahman et al., 2002 as *Psychrobacillus insolitus* comb. nov., *Psychrobacillus psychrotolerans* comb. nov. and *Psychrobacillus psychrodurans* comb. nov. Syst. Appl. Microbiol. 33, 367-373

Kumar, P. K., Joshi, P., Bisht, J. K. et al. 2011. Cold-Tolerant Agriculturally Important Microorganisms. In: Plant Growth and Health Promoting Bacteria. Microbiology Monographs. Volume 18, 2011, pp 273-296.

López-Bucio, J., Campos-Cuevas, J. C., Hernández-Calderón, E. et al. 2007. *Bacillus megaterium* rhizobacteria promote growth and alter root-system architecture through an auxin- and ethylene-independent signaling mechanism in *Arabidopsis thaliana*. Mol. Plant Microbe Interact. 20, 207-217

Mishra, P. K., Bisht, S. C., Bisht, J. K., Bhatt, J. C. 2012. Cold-tolerant PGPRs as bioinoculants for stress management. In: Maheshwari D K (ed). Bacteria in agrobiology: Stress Management, DOI 10.1007/978-3-642-23465-1_6, # Springer-Verlag Berlin Heidelberg Nakamura, L. K. 1989. Taxonomic relationship of black-pigmented *Bacillus subtilis* strains and a proposal for *Bacillus atrophaeus* sp. nov. Int. J. Syst. Bacteriol. 39, 295-300.

Prevost D, Drouin P, Laberge S, et al. 2003. Cold-adapted rhizobia for nitrogen fixation in temperate regions. Can. J. Bot. 81, 1153-1161

Schwartz, A. R., Ortiz, I., Maymon, M. et al. 2013. *Bacillus simplex*—A little known PGPB with anti-fungal activity-alters pea legume root architecture and nodule morphology when coinculated with *Rhizobium leguminosarum* bv. *viciae*. Agronomy 3, 595-620

Selvakumar, G., Kundu, S., Joshi, P. et al. 2008a. Characterization of a cold-tolerant plant growth-promoting bacterium *Pantoea dispersa* 1A isolated from a sub-alpine soil in the North Western Indian Himalayas. World J. Microbiol. Biotechnol. 24, 955-960

Selvakumar, G., Mohan, M., Kundu, S. et al. 2008b. Cold tolerance and plant growth promotion potential of *Serratia marcescens* strain SRM (MTCC 8708) isolated from flowers of summer squash (*Cucurbita pepo*). Lett. Appl. Microbiol. 46:171-175

Zhang, H., Prithiviraj, B., Charles, T. C. et al. 2003. Low temperature tolerant *Bradyrhizobium japonicum* strains allowing improved nodulation and nitrogen fixation of soybean in a short season (cool spring) area. Eur. J. Agron. 19, 205-213

The invention claimed is:

1. A method of stimulating the growth of cultivated plants, comprising treating said plants with a cold-tolerant *Bacillus* strain, wherein the cold-tolerant *Bacillus* strain comprises a *Bacillus atrophaeus* species and a *Bacillus simplex* species, and wherein the cold-tolerant *Bacillus simplex* species comprises ABI02S1 DSM 32020 or ABI12 DSM 32283, or a mixture thereof.

2. The method according to claim 1, wherein the cold-tolerant *Bacillus* strain comprises a *Bacillus atrophaeus* species, and wherein the *Bacillus atrophaeus* species comprises ABI02A1 DSM 32019, ABI03 DSM 32285, or ABI0S DSM 29418, or a mixture thereof.

3. The method according to claim 1, wherein the cold-tolerant *Bacillus* strain is formulated as a fluid spore suspension.

4. The method according to claim 1, wherein said treating comprises treating seeds during planting or treating seeds after planting.

5. The method according to claim 1, wherein the cold-tolerant *Bacillus* strain is formulated as a dry preparation ("dry stain").

6. The method according to claim 1, wherein the method further comprises treating said plants with humic acid.

7. The method according to claim 1, wherein the method further comprises treating said plants with a plant growth promoting fungus *Trichoderma* sp.

8. The method according to claim 3, wherein the fluid spore suspension comprises at least $2\times10^9$ spores/ml.

9. The method according to claim 3, wherein the fluid spore suspension comprises at least $1\times10^{10}$ spores/ml.

10. The method according to claim 7, wherein said treating is by pour administration or by spray administration.

11. The method according to claim 5, wherein the cold-tolerant *Bacillus* strain is formulated with at least $5\times10^9$ spores/ml.

12. The method according to claim 5, wherein the cold-tolerant *Bacillus* strain is formulated with at least $2\times10^{10}$ spores/ml.

13. A method of stimulating the growth of cultivated plants, comprising treating said plants with a cold-tolerant *Bacillus* strain, wherein the cold-tolerant *Bacillus* strain comprises a *Bacillus atrophaeus* species or a *Bacillus simplex* species or a mixture thereof, and wherein the cold-tolerant *Bacillus simplex* species comprises ABI02S1 DSM 32020 or ABI12 DSM 32283, or a mixture thereof, wherein the cold-tolerant *Bacillus* strain comprises a cold-tolerant *Bacillus* strain comprising *Bacillus atrophaeus* ABI02A1 DSM 32019, ABI03 DSM 32285, or ABI0S DSM 29418.

\* \* \* \* \*

SEQUENCE LISTING

```
<160> NUMBER OF SEQ ID NOS: 6

<210> SEQ ID NO 1
<211> LENGTH: 27
<212> TYPE: DNA
<213> ORGANISM: Artificial Sequence
<220> FEATURE:
<223> OTHER INFORMATION: Primer pRB1601
<220> FEATURE:
<221> NAME/KEY: misc_feature
<223> OTHER INFORMATION: pRB1601

<400> SEQUENCE: 1
ggatcctaat acatgcaagt cgagcgg                                              27

<210> SEQ ID NO 2
<211> LENGTH: 28
<212> TYPE: DNA
<213> ORGANISM: Artificial Sequence
<220> FEATURE:
<223> OTHER INFORMATION: Primer pRB1602
<220> FEATURE:
<221> NAME/KEY: misc_feature
```

```
<223> OTHER INFORMATION: pRB1602

<400> SEQUENCE: 2
ggatccacgt attaccgcgg ctgctggc                                      28

<210> SEQ ID NO 3
<211> LENGTH: 21
<212> TYPE: DNA
<213> ORGANISM: Artificial Sequence
<220> FEATURE:
<223> OTHER INFORMATION: Primer gyrFW
<220> FEATURE:
<221> NAME/KEY: misc_feature
<223> OTHER INFORMATION: gyrFW

<400> SEQUENCE: 3
cagtcaggaa atgcgtacgt c                                             21

<210> SEQ ID NO 4
<211> LENGTH: 21
<212> TYPE: DNA
<213> ORGANISM: Artificial Sequence
<220> FEATURE:
<223> OTHER INFORMATION: Primer gyrRV
<220> FEATURE:
<221> NAME/KEY: misc_feature
<223> OTHER INFORMATION: gyrRV

<400> SEQUENCE: 4
caaggtaatg ctccaggcat t                                             21

<210> SEQ ID NO 5
<211> LENGTH: 35
<212> TYPE: DNA
<213> ORGANISM: Artificial Sequence
<220> FEATURE:
<223> OTHER INFORMATION: Primer cheAFW
<220> FEATURE:
<221> NAME/KEY: misc_feature
<223> OTHER INFORMATION: cheAFW

<400> SEQUENCE: 5
gaaacggaka yatggmagtb acmtcaract ggctg                              35

<210> SEQ ID NO 6
<211> LENGTH: 35
<212> TYPE: DNA
<213> ORGANISM: Artificial Sequence
<220> FEATURE:
<223> OTHER INFORMATION: Primer cheARV
<220> FEATURE:
<221> NAME/KEY: misc_feature
<223> OTHER INFORMATION: cheARV

<400> SEQUENCE: 6
tgctcragac gcccgcggwc aatgacaagc tcttc                              35
```